(12) United States Patent
Harada et al.

(10) Patent No.: US 7,964,637 B2
(45) Date of Patent: Jun. 21, 2011

(54) PROCESS FOR PRODUCING OPTICALLY ACTIVE THEASPIRANE

(75) Inventors: Makoto Harada, Hiratsuka (JP); Hiroyuki Matsuda, Kanagawa (JP); Kenya Ishida, Kanagawa (JP); Yuichiro Yamazaki, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 701 days.

(21) Appl. No.: 11/992,067

(22) PCT Filed: Sep. 8, 2006

(86) PCT No.: PCT/JP2006/317876
§ 371 (c)(1),
(2), (4) Date: Mar. 13, 2008

(87) PCT Pub. No.: WO2007/032279
PCT Pub. Date: Mar. 22, 2007

(65) Prior Publication Data
US 2009/0270516 A1 Oct. 29, 2009

(30) Foreign Application Priority Data
Sep. 13, 2005 (JP) .................................. 2005-264678

(51) Int. Cl.
*A61K 31/335* (2006.01)
*C07D 307/94* (2006.01)
(52) U.S. Cl. ........................................ 514/462; 549/345
(58) Field of Classification Search ............... 514/462; 549/345
See application file for complete search history.

(56) References Cited

U.S. PATENT DOCUMENTS
4,011,246 A    3/1977   Markezich

FOREIGN PATENT DOCUMENTS
JP    60-1119    1/1985

OTHER PUBLICATIONS

H. Masuda et al., "A Short-Step Synthesis of Theaspirane", Agric. Biol. Chem., 49(3), pp. 861-862 (1985).
Schmidt et al., Journal of Agricultural and Food Chemistry, 40(7):1188-1191 (1992).
Winterhalter et al., Journal of Agricultural and Food Chemistry, 36(3):560-562 (1988).
Full et al., MDGC-MS: A Powerful Tool for Enantioselective Flavor Analysis, HRC, 16(11):642-644 (1993).
Boulin et al., Tetrahedron, 56(24):3927-3932 (2000).
Yaguchi et al., "CHIRAROMA" analysis (2): Passionfruit no Tokucho Koki Seibun, Dai 49 Kai Koryo Terpene Oyobi Seiyu Kagaku ni Kansuru Toronkai Koen Yoshishu, Nov. 1, 2005, pp. 45-46.

*Primary Examiner* — Taofiq A Solola
(74) *Attorney, Agent, or Firm* — Peter F. Corless; Christine C. O'Day; Edwards Angell Palmer & Dodge LLP

(57) ABSTRACT

A simplified production method of stereoisomer of theaspiran having high optical purity has been desired. An alcohol compound having a specific skeleton is enantioselectively esterified with an enzyme, or an ester compound having a specific skeleton is enantioselectively hydrolyzed with an enzyme. The resultant optically active ester or optically active alcohol is used. Thus, optically active theaspiran having a desired configuration and having a high optical purity is obtained in a satisfactory yield.

9 Claims, No Drawings

PROCESS FOR PRODUCING OPTICALLY ACTIVE THEASPIRANE

TECHNICAL FIELD

The present invention relates to a method for producing optically active theaspiran which is useful as a flavor or fragrance component, and an aromatic composition comprising optically active theaspiran.

BACKGROUND OF THE INVENTION

Theaspiran[2,6,10,10-tetramethyl-1-oxa-spiro[4,5]-deca-6-en] is a compound known as a flavor component which is contained in a minute amount in various essential oils such as raspberry oil and passion fruit oil (Non-patent Literature 1), especially it has been known to be useful as a aromatic flavor component (Patent Literature 1). However, theaspiran has asymmetric carbons at the second position and fifth position, giving 4 stereoisomers, and the mixture ratio of the isomers has been known to vary depending on a source of the essential oils (Non-patent Literature 2 and Non-patent Literature 3). In the circumstances, various processes for the production of theaspiran have been studied (Patent Literature 2, Patent Literature 3, etc.); however, their products are racemates, while a synthesis of an optically active compound reported in Non-patent Literature 2 comprises esterification by chiral phenyl propionic acid and HPLC separation, thereby the synthesis was usable for microsynthesis but not for practical use. Therefore, an inexpensive method for industrial production of theaspiran as a flavor component has been desired.

Non-patent Literature 1: Helv. Chim. Acta 57, 1301 (1974)
Non-patent Literature 2: J. Agric. Food Chem., 40, 1188 (1992)
Non-patent Literature 3: Z. Lebensm. Unters. Forsch., 196, 307 (1993)
Patent Literature 1: JP-A-60-1119
Patent Literature 2: JP-A-53-92757
Patent Literature 3: JP-A-61-134386

DISCLOSURE OF THE INVENTION

Problem to be Solved by the Invention

Accordingly, conventional methods have difficulties in obtaining a desired stereoisomer of theaspiran selectively; therefore, development of a simplified production method of stereoisomer of theaspiran having high optical purity has been desired.

Means of Solving the Problems

The present inventors were dedicated to studying for solving said problem and it resulted in finding that optically active theaspiran having a desired configuration can be obtained in high optical purity and good yield by using an optically active ester compound or alcohol compound which is obtained by stereoselective esterification of an alcohol compound having a specific skeleton or stereoselective hydrolysis of ester compound having a specific skeleton by using an enzyme, and the present invention has been completed.

That is, the present invention includes [1] through [11] as below.

[1] A method for producing optically active theaspiran represented by the formula (4*)

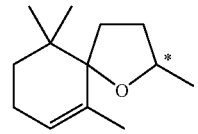

wherein * indicates asymmetric carbon atom:

the method is characterized in that mixture of optical isomers of alcohol represented by the formula (1)

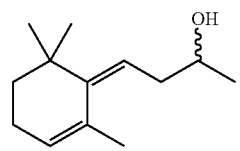

is enantioselectively esterified in the presence of an enzyme by an esterification agent of the general formula (2)

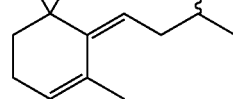

wherein $R^1$ is a hydrogen atom or $C_1$-$C_6$ hydrocarbon group optionally having a substituent group, and $R^2$ is a hydrogen atom, $C_1$-$C_6$ alkyl group or $C_1$-$C_4$ alkoxy group;

and optically active ester represented by the general formula (3*) and/or optically active alcohol represented by the formula (1*) is obtained

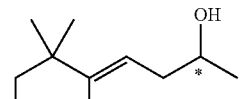

wherein $R^1$ is a hydrogen atom or a $C_1$-$C_6$ hydrocarbon group optionally having a substituent group; wherein * indicates an asymmetric carbon atom; and the abundance ratio of R-form and S-form of the formula 3* and the said ratio of the formula 1* are different from each other, one contains more R-form and the other contains more S-form) the resulting optically active alcohol (1*) is isolated, and the alcohol (1*) is cyclized by an acid catalyst.

[2] Method for producing optically active theaspiran represented by the formula (4*) wherein * indicates the same as above-mentioned:

(4*)

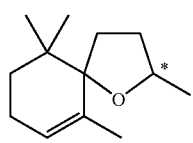

the method is characterized in that the optically active ester represented by the general formula (3*) which is obtained by the method of [1] is isolated, hydrolyzed and cyclized by an acid catalyst.

[3] The method for producing optically active theaspiran represented by the formula (4*)

(4*)

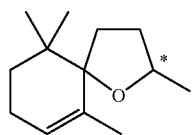

wherein * indicates the same as above-mentioned:
the method is characterized in that mixture of optical isomers of ester represented by the formula (3)

(3)

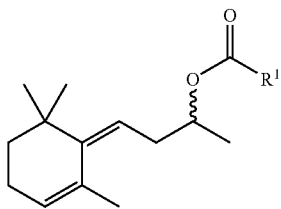

wherein $R^1$ is a hydrogen atom or a $C_1$-$C_6$ hydrocarbon group optionally having a substituent group;
is enantioselectively hydrolyzed in the presence of an enzyme and optically active ester represented by the general formula (3*) and/or optically active alcohol represented by the formula (1*) is obtained (3*)

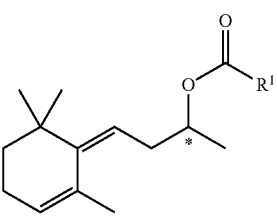

(1*)

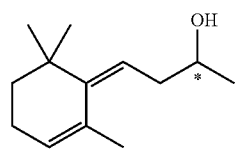

wherein $R^1$ is a hydrogen atom or a $C_1$-$C_6$ hydrocarbon group optionally having a substituent group; wherein * indicates the same as above-mentioned; and the abundance ratio of R-form and S-form of the formula (3*) and the said ratio of the formula (1*) are different from each other, one contains more R-form and the other contains more S-form the resulting optically active alcohol of the formula (1*) is isolated, and the alcohol (1*) is cyclized by an acid catalyst.

[4] A method for producing an optically active theaspiran represented by the formula (4*) wherein * indicates the same as above-mentioned:

(4*)

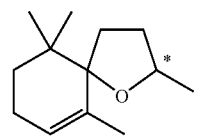

the method is characterized in that the optically active ester represented by the general formula (3*) which is obtained by the method of [3] is isolated and hydrolyzed, and then cyclized by the acid catalyst.

[5] The method for producing an optically active theaspiran according to any of [1]-[4] characterized in that the enzyme is lipase.

[6] An aromatic composition characterized by containing optically active theaspiran according to any of [1]-[5] at 0.000001-10 wt %.

[7] Food and beverage, cosmetics and groceries characterized by containing an aromatic composition according to [6].

[8] Use of optically active theaspiran according to any of [1]-[5] for producing aromatic composition.

[9] A method for aromatic composition characterized in that an optically active theaspiran is produced by the method according to any of [1]-[5], and said theaspiran is mixed with a carrier which is acceptable in manufacturing aroma chemical and/or other aromatic composition.

[10] Use of optically active theaspiran according to any of [1]-[5] for producing food and beverage, cosmetics and groceries.

[11] A method for producing food and beverage, cosmetics and groceries characterized by producing an optically active theaspiran by the method according to any of [1]-[5] and adding the said optically active theaspiran.

The following is to provide a detailed description of the present invention.

Racemate of an alcohol compound represented by the formula (1) which is a precursor of the invention can be synthesized according to a known method (U.S. Pat. No. 4,011,245, etc). That is, it can be easily synthesized from β-Ionone by enol esterification followed by a reduction reaction shown below.

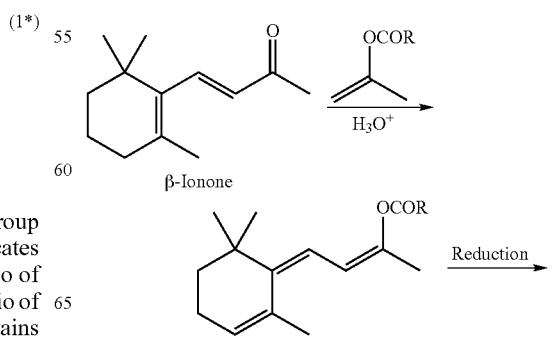

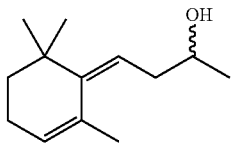

Then, the following is to describe enantio selective esterification of the present invention.

A preferable enzyme used in the present invention is a hydrolase, for example lipase and the like. These enzymes are generally commercially available.

Specific examples of the enzyme suitable for use in the present invention include lipases originated from *Aspergillus niger, Mucor javanicus, Pseudomonas aeruginosa, Pseudomonas cepasia, Pseudomonas fluorescence, Rhizopus delemar, Rhizopus niveus, Rhizomucor miehei, Candida antarctica, Candida rugosa, Geotrichum candidum, Penicillium cyclopium, Penicillium roqueforti, Mucor miehei*, etc.

Particularly preferable hydrolase used in the present invention is, for example, lipase originated from *Candida antarctica*.

A hydrolase used in a method of the present invention may be free enzyme or supported enzyme which is immobilized by insoluble carrier. It is preferable to use carrier-immobilized enzyme because of easiness and for repeated use.

Any carrier which can immobilize an enzyme is preferred for use, for example, a natural polymeric material such as chitosan and dextran; a synthetic resin material such as polyacryl amide, acetyl cellulose, and polyimide; a silicate crystallite mesoporous material, ceramics, porous glass and those in the form of bead, etc. Example of carrier-immobilizing method include carrier binding method, crosslinking method, entrapping method. Examples of hydrolase preferable to be used in a method of the present invention include a lipase originated from *Candida antarctica*, CHIRAZYME L2 (Roche), Novozyme 435 or Novozyme SP 435 (Novo Nordisk).

Esterification by an enzyme in the present invention can be performed without solvent; however, it is preferable to use a solvent. Examples of the solvents which can be used include, but not limited to: hydrocarbons, for example, pentane, hexane, heptane, toluene, xylene and the like; halogenated hydrocarbons, for example, dichloromethane, 1,2-dichloroethane, chloroform, carbon tetrachloride, o-dichlorobenzene and the like; ethers, for example, diethyl ether, diisopropyl ether, tert-butyl methyl ether, dimethoxy ethane, ethylene glycol diethyl ether, tetrahydrofuran, 1,4-dioxane and the like; ketones, for example, acetone, methyl ethyl ketone and the like; amides, for example, N,N-dimethyl formamide, N,N-dimethyl acetoamide, N-methylpyrrolidone and the like; sulfoxides, for example, dimethyl sulfoxide and the like; nitriles, for example, acetonitrile, propionitrile and the like. These solvents can be used alone or in a combination of two or more.

More preferable solvent among these includes heptane and toluene. The amount of such a solvent used is 1 to 100 times for the mount of the alcohol represented by the general formula (1), preferably 5 to 50 times.

The reaction temperature must be suitable for the activity of the enzyme, preferably 80° C. or lower, more preferably 0° C. to 50° C. The reaction time is usually from 1 hour to 1 week, preferably from 3 hours to 3 days.

Example of $C_1$-$C_6$ hydrocarbon group which optionally has a substituent represented by $R^1$ of the esterification agent of the general formula (2) used in the present invention includes a straight or branched chain or cyclic alkyl group or a phenyl group.

The alkyl group includes a straight or branched chain or cyclic alkyl group, for example, methyl group, ethyl group, n-propyl group, isopropyl group, n-butyl group, sec-butyl group, isobutyl group, tert-butyl group, n-pentyl group, and a hexyl group, and include cyclic alkyl group, for example, cyclopentyl group, methyl cyclopentyl group, and a cyclohexyl group.

These alkyl groups optionally have a substituent such as aryl groups, alkoxyl groups, and halogen atoms, etc.

Example of substituted aryl groups of the alkyl group includes phenyl groups, tolyl groups, anisyl group, a chlorophenyl group, and a naphthyl group.

Example of substituted alkoxy groups of the alkyl group includes straight or branched chain or cyclic alkyl groups, for example, $C_{1-4}$ alkoxy group, such as methoxy group, ethoxy group, n-propoxy group, isopropoxy group, an n-butoxy group, 2-butoxy group, isobutoxy group and tert-butoxy group.

Example of substituted halogen atoms of the alkyl group includes fluorine and chorine. Also, a substituent of phenyl group represented by $R^1$ which optionally has a substituent includes alkyl groups, alkoxy groups, nitro group and halogen atoms as mentioned above.

Example of $C_1$-$C_6$ alkyl group and alkoxy group represented by $R_2$ of the esterification agent represented by the general formula (2) used in the present invention includes the groups exemplified for $R^1$.

Specific examples for the esterification agent represented by the general formula (2) of the present invention includes vinyl esters such as vinyl acetate, vinyl propionate, vinyl butyrate, and vinyl benzoate; isopropenyl esters such as isopropenyl acetate, isopropenyl butyrate, and isopropenyl benzoate; 1-ethoxyvinyl esters such as 1-ethoxyvinyl acetate, 1-ethoxyvinyl benzoate. Particularly, the acyl group having three or more carbon atoms such as the propionyl of vinyl propionate, the butyryl of vinyl butyrate, and the butyryl of isopropenyl butyrate, are preferable. Also, these esterification agents can be used as a solvent.

In the enantio selective esterification reaction of the present invention, depending on reaction condition of enzymes and esterification agent, (R) rich ester (3-R) and (S) rich alcohol (1-S), or (S) rich ester (3-S) and (R) rich alcohol (1-R) can be synthesized respectively

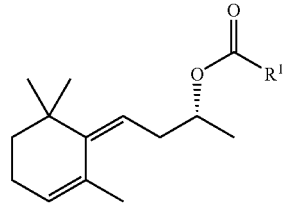

(3-R)

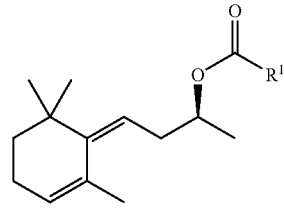

(3-S)

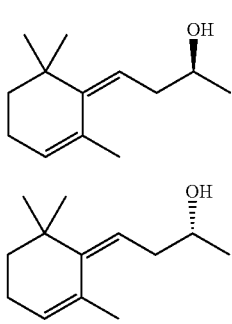

wherein, $R^1$ indicates the same group as mentioned above.

The enantio selective hydrolysis of esters represented by the general formula (3) in a production method of the present invention is described as follows.

An enzyme used for the enantio selective hydrolysis includes enzymes mentioned above, particularly lipase is preferable.

The hydrolysis reaction of the present invention is usually performed in a system comprising a phosphate buffer alone or together with an organic solvent.

Specific example of the organic solvent used in the reaction includes, but not limited to, aliphatic hydrocarbons such as, for example, pentane, hexane, heptane, octane, and cyclohexane; aromatic hydrocarbons such as, for example, benzene, toluene and xylene; halogenated hydrocarbons such as, for example, dichloromethane, 1,2-dichloroethane, chloroform, carbon tetrachloride, and o-dichlorobenzene; ethers such as, for example, diethyl ether, diisopropyl ether, tert-butyl methyl ether, dimethoxy ethane, ethylene glycol diethyl ether, tetrahydrofuran, and 1,4-dioxane; ketones such as, for example, acetone and methyl ethyl ketone; amides such as, for example, N,N-dimethyl formamide, N,N-dimethyl acetoamide, and N-methylpyrrolidone; sulfoxides such as, for example, dimethyl sulfoxide; nitrites such as, for example, acetonitrile and propionitrile. These solvents can be used alone or in a combination of two or more solvents.

Particularly, examples of a preferred solvent include phosphate buffer solution or mixture solvent of phosphate buffer solution and tetrahydrofuran, acetone or acetonitrile and the like.

The amount of a hydrolase used is 0.01 to 100 wt %, preferably 0.1 to 50 wt %, of ester compounds represented by the general formula (3).

The reaction temperature must be suitable for the activity of enzymes, preferably 80° C. or lower, more preferably 0° C. to 50° C. The liquid property of the reaction solution is pH about 3.0 to 10, preferably pH about 6.0 to 8.0. Adjustment of the liquid property can be made with, for example, aqueous solution of potassium dihydrogen phosphate, aqueous solution of dipotassium hydrogen phosphate and the like.

The reaction time is generally from 1 hour to 1 week, preferably from 4 hours to 3 days.

The enzyme used in the reaction can be removed by a treatment such as filtration or separation after the completion of the reaction, and the enzyme can be reused several times after filtration when the enzyme is immobilized by insoluble carrier.

In the enantio selective hydrolysis of the present invention, depending on type of an enzyme used for the reaction and reaction condition of enantio selective hydrolysis, (R) rich ester (3-R) and (S) rich alcohol (1-S), or (S) rich ester (3-S) and (R) rich alcohol (1-R) can be synthesized respectively.

The optically active ester compound represented by the general formula (3*) and the optically active alcohol compound represented by the general formula (1*), which are enantio selectively esterified or enantio selectively hydrolyzed, can be separated and purified by the ordinary methods such as distillation, extraction, recrystallization or column chromatography, after the enzyme is removed by filtration, centrifugation or the like, or without removal of the enzyme.

Also, the optically active ester compound which is separated can be converted to an optically active alcohol compound by the ordinary hydrolysis.

A process of production of optically active theaspiran by ring closure of an optically active alcohol obtained in the process described above is explained as follows.

The acid catalyst used in this process includes an organic or inorganic proton acid such as hydrochloric acid, sulfuric acid, phosphoric acid, paratoluenesulfonic acid, naphthalenesulfonic acid, and the like, particularly paratoluenesulfonic acid is preferable.

Example of the reaction solvent includes aliphatic hydrocarbons such as, pentane, hexane, heptane, octane, and cyclohexane; aromatic hydrocarbons such as, toluene and xylene; halogenated hydrocarbons such as, dichloromethane, 1,2-dichloroethane, chloroform, carbon tetrachloride, and o-dichloro benzene; ethers such as, diethyl ether, diisopropyl ether, tert-butyl methyl ether, dimethoxyethane, ethylene glycol diethyl ether, tetrahydrofuran, and 1,4-dioxane, particularly aromatic hydrocarbons such as toluene and xylene is preferable.

The reaction temperature may be from 0° C. to 120° C., preferably from 50° C. to 100° C. The reaction time can usually be from 1 hour to 10 hours, preferably from 2 to 5 hours.

The resulting optically active theaspiran can be purified by for example distillation, and polymerization inhibitors or antioxidant additives and the like can be added in order to prevent decomposition, polymerization or the like of the optically active theaspiran during distillation. Examples of the polymerization inhibitors or antioxidant additives used include phenols such as butyl hydroxytoluene (BHT), butyl hydroxyanisole (BHA), dibutyl ethyl phenol (DBEP), and 4-methoxyphenol, α-tocopherol, isopropyl citrate, nordihydroguaiaretic acid, propyl gallate, and the like.

Naturally, theaspiran (R) is obtained by using (3-R) compound of an optically active alcohol compound for ring closure while theaspiran (S) is obtained by using (3-S) compound of an optically active alcohol compound for ring closure.

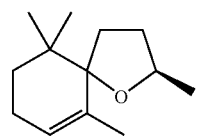

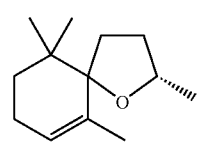

The optically active theaspiran (R) produced according to the present invention has aroma of fruits, peach and honey, and sweet scent, while the optically active theaspiran (S) produced according to the present invention has aroma of camphor, mint, wood, and eucalyptus, which are clearly different from the racemate, and they can be used directly to flavor or fragrance various products, or mixed with other components to form aromatic composition and use the composition to flavor or fragrance various products.

Examples of the other flavoring or perfuming component which can be used together with the optically active theaspiran include various synthetic perfume, natural essential oils, synthetic essential oils, citrus oils, animal perfume, and the like.

The synthetic perfume which can be contained are not limited as long as it is conventionally used for flavoring or perfuming; for example, at least one or more of synthetic perfume selected from a group consisting of esters, alcohols, aldehydes, ketones, phenols, ethers, lactones, hydrocarbons, compounds containing nitrogen, compounds containing sulfur, and acids, described in "Synthetic Fragrance and Flavor: Chemistry and Product Knowledge" (Motoichi INDO, published by Chemical Daily Co., Ltd.) and the like.

Examples of the esters include propyl formate, butyl formate, amyl formate, octyl formate, linalyl formate, citronellyl formate, geranyl formate, neryl formate, terpinyl formate, ethyl acetate, isopropyl acetate, isoamyl acetate, hexyl acetate, cis-3-hexenyl acetate, trans-2-hexenyl acetate, octyl acetate, nonyl acetate, decyl acetate, dodecyl acetate, dimethyl undecadienyl acetate, styrallyl acetate, ocimenyl acetate, myrcenyl acetate, dihydro myrcenyl acetate, linalyl acetate, citronellyl acetate, geranyl acetate, neryl acetate, tetrahydro-mugol acetate, lavandulyl acetate, nerolidol acetate, dihydrocuminyl acetate, terpinyl acetate, citril acetate, nopyl acetate, dihydroterpinyl acetate, 2,4-dimethyl-3-cyclohexenyl methyl acetate, myraldyl acetate, veticol acetate, decenyl propionate, linalyl propionate, geranyl propionate, neryl propionate, terpinyl propionate, tricyclodecenyl propionate, styrallyl propionate, anisil propionate, octyl butyrate, neryl butyrate, cinnamyl butyrate, isopropyl isobutyrate, octyl isobutyrate, linalyl isobutyrate, neryl isobutyrate, linalyl isovalerate, terpinyl isovalerate, phenylethyl isovalerate, 2-methylpentyl 2-methylvalerate, ethyl haxanoate, hexyl hexanoate, methyl 3-hydroxyhexanoate, ethyl 3-hydroxyhexanoate, methyl octanoate, octyl octanoate, linalyl octanoate, methyl nonanoate, methyl undecylenate, linalyl benzoate, methyl cinnamate, isoprenyl angelicate, methyl gelanate, triethyl citrate, ethyl acetoacetate, ethyl 2-hexylacetoacetate, ethyl benzyl-acetoacetate, ally 2-ethylbutyrate, ethyl 3-hyoxybutyrate, ethyl nonanoate, ethyl decanoate, propyl 2,4-decadienoate, propyl 2,4-decadienoate, methyl anthranylate, ethyl N-methyl-anthranylate, and the like.

Examples of the alcohols include 3-heptanol, 1-nonanol, 1-undecanol, 2-undecanol, 1-dodecanol, prenol, 10-undecen-1-ol, dihydrolinalool, tetrahydromugol, myrcenol, dihydromyrcenol, tetrahydromyrcenol, ocimenol, terpineol, hotrienol, 3-thuyanol, benzylalcohol, β-phenylethyl alcohol, α-phenylethyl alcohol, 3-methyl-1-pentanol, 1-heptanol, 2-heptanol, 1-octanol, 3-octanol, 1-nonanol, 2-nonanol, 2,6-dimethyl-heptanol, 1-decanol, trans-2-hexenol, cis-3-hexenol, methyltrimethylcyclopentenylbutenol, citronellol, dihydro-myrcenol, rhodinol, geraniol, nerol, linalool, tetrahydrolinalool, dimethyloctanol, hydroxycitronellol, isopulegol, menthol, terpineol, dihydro-terpineol, carveol, dihydro-carveol, perilla alcohol, 4-thuyanol, myrtenol, fenchyl alcohol, farnesol, nerolidol, cedrenol, anisealcohol, 3-phenyl-propyl alcohol, cinnamic alcohol, amylcinnamic alcohol, etc.

Examples of the aldehydes include, acetaldehyde, n-hexanal, n-heptanal, n-octanal, n-nonanal, 2-methyloctanal, 3,5,5-trimethylhexanal, decanal, undecanal, 2-methyldecanal, dodecanal, tridecanal, tetradecanal, trans-2-hexenal, trans-4-decenal, cis-4-decenal, trans-2-decenal, 10-undecenal, trans-2-undecenal, trans-2-dodecenal, 3-dodecenal, trans-2-tridecenal, 2,4-hexadienal, 2,4-decadienal, 2,4-dodecadienal, 5,9-dimethyl-4,8-decadienal, citral, dimethyloctanal, α-methylene citronellal, citronellyl oxyacetaldehyde, myrtenal, neral, phenyl acetoaldehyde, octanal dimethyl acetal, nonanal dimethyl acetal, decanal dimethyl acetal, decanal diethyl acetal, 2-methyl undecanal dimethyl acetal, citral dimethyl acetal, citral diethyl acetal, citral propylene glycol acetal, n-valeraldehyde, iso-valeraldehyde, 2-methyl butanal, 2-pentenal, trans-2-heptenal, trans-2-nonenal, 2,6-dimethyl-5-heptenal, 2,4-undecadienal, trimethyl decadienal, citronellal, hydroxyl citronellal, safranal, vernaldehyde, benzaldehyde, p-isopropyl-phenyl acetoaldehyde, p-methyl-hydrotropaldehyde, phenyl propionaldehyde, 2-methyl-3-(4-methyl phenyl)-propanal, cycramenaldehyde, cinnamicaldehdye, salicylaldehyde, anisaldehyde, p-methyl-phenoxyacetaldehyde, acetaldehyde diethyl acetal, citronellyl methyl acetal, acetaldehyde 2-phenyl-2,4-pentandiol acetal, 2-hexenal diethyl acetal, cis-3-hexenal diethyl acetal, heptanal diethyl acetal, 2-hexyl-5-methyl-1,3-dioxolane, citronellal-cyclo-mono-glycol acetal, hydroxyl-citronellal dimethyl acetal, phenyl acetaldehyde dimethyl acetal, and the like.

Examples of the ketones include, 2-pentanone, 3-hexanone, 2-heptanone, 3-heptanone, 4-heptanone, 2-octanone, 3-octanone, 2-nonanone, 2-undecanone, methyl heptenone, dimethyl octenone, geranyl acetone, farnesyl acetone, 2,3,5-trimethyl-4-cyclohexenyl-1-methyl ketone, nerone, nootkatone, dihydronootkatone, acetophenone, 4,7-dihydro-2-isopentyl-2-methyl-1,3-dioxepin, 2-pentanone, 3-hexanone, 2-heptanone, 2,3-hexanedione, 3-nonanone, ethyl isoamyl ketone, diacetyl, amyl-cyclopentenone, 2-cyclopentyl cyclopentanone, hexyl cyclopentanone, heptyl cyclopentanone, cis-jasmone, dihydro-jasmone, trimethyl pentyl cyclopentanone, 2-(2-(4-methyl)-3-cyclohexanone-1-yl)-propyl-cyclopentanone, α-damascone, β-damascone, α-dynascone, trimethyl cyclohexenyl butenone, β-damasenone, jonan (ionone), methylionone, allylionone, cashmeran, L-carvone, menthone, camphor, 2,5-dimethyl-4-hydroxy-3-(2H)-furanone, p-methyl acetophenone, p-methoxy-acetophenone, benzylidene acetone, raspberry ketone, methyl naphtyl ketone, benzophenone, furfural acetone, homofuronol, maltol, ethyl maltol, acetoacetic acid ethyl ethyleneglycol ketal, and the like.

Examples of the phenol derivatives include thymol, carvacrol, β-naphthol isobutyl ether, anethole, β-naphthol methyl ether, β-naphthol ethyl ether, veratrole, hydroquinone dimethyl ether, 2,6-dimethoxyl phenol, 4-ethyl guaiacol, eugenol, ethyl isoeugenol, tert-butyl hydroquinone dimethyl ether, and the like.

Examples of the ethers include decyl vinyl ether, α-terpinyl methyl ether, iso-proxen, 2,2-dimethyl-5-(1-methyl-1-propenyl)-tetrahydro-furan, rosefuran, 1,4-cineol, nerol oxide, 2,2,6-trimethyl-6-vinyl tetrahydro-pyran, methyl hexyl ether, ocimene epoxide, limonene oxide, rhubofix, caryophyllene oxide, linalool oxide, 5-isopropenyl-2-methyl-2-vinyl tetrahydro-furan, nerol oxide, rose oxide, and the like.

Examples of the lactones include γ-undecalactone, δ-dodecalactone, γ-hexylactone, γ-nonalactone, γ-decalactone, γ-dodecalactone, jasmine lactone, methyl γ-decalactone, 7-decenolactone, jasmolactone, propylidene phthalide, δ-hexylactone, δ-2-decenolactone, dodecalactone, dihydrocoumarin, coumarin, and the like.

Examples of the hydrocarbons include ocimene, limonene, α-phellandrene, terpinene, 3-caren, bisabolene, valencene, alloocimene, myrcene, farnesene, α-pynene, β-pynene, camphene, terpinolene, paracymene, cedrene, β-caryophyllene, cadinene, and the like.

Examples of the compounds containing nitrogen or sulfur include methyl anthranilate, ethyl anthranilate, methyl N-methyl-anthranilate, methyl N2-methyl-pentylidyne-anthranilate, ligantral, dodecane nitrile, 2-tridecene nitrile, geranyl nitrile, citronellyl nitrile, 3,7-dimethyl-2,6-nonadieno nitrile, indole, 5-methyl-3-heptanone oxime, limonene thiol, 1-P-menthen-8-thiol, butyl anthranilate, cis-3-hexenyl anthranilate, phenyl ethyl anthranilate, cinnamyl anthranilate, dimethyl sulfide, 8-mercaptomenthone, 2-methyl-4-propyl-1,3-oxathiane, and the like.

Examples of the acids include acetic acid, propionic acid, butyric acid, valeric acid, hexanoic acid, octanoic acid, decanoic acid, 2-decenoic acid, geranoic acid, 2-methyl-butyric acid, 2-ethyl-butyric acid, phenyl-acetic acid, cinnamic acid, iso-butyric acid, iso-valeric acid, 3-methyl valeric acid, 2-hexenoic acid, 2-methyl-2-pentenoic acid, 2-methyl-heptanoic acid, myristic acid, stearic acid, lactic acid, pyruvic acid, cyclohexane-carbonic acid, and the like.

Also, preferable examples of the natural aroma chemical include one or more selected from sweet orange, bitter orange, neroli, mandarin, petit grain, bergamot, tangerine, onshuu mandarin orange, daidai, hassaku, iyokan, lemon, lime, grape fruit, yuzu (*Citrus junos*), sudachi (*Citrus sudachi*), cabosu (*Citrus sphaerocarpa*), sweety and the like.

Also, the following can also be used other than the above as aroma substance or aroma improving agent; for example, citronella, elemi, olibanum, marjoram, angelica root, star anise, basil, hay, calamos, caraway, cardamom, pepper, cascarilla, ginger, sage, clary sage, clove, coriander, eucalyptus, fennel, pimento, juniper, fenugreek, laurel, mace, sugi (cedar), senkyu, almond, apple mint, anise, artemisia, apricot, ambrette, strawberry, fig, ylang-ylang, winter green, ume apricot, elder, enju (Japanese-pagota tree), oak moss, allspice, orris, currant, cassie, chamomile, galanga, Chinese quince, gambir, guava, gooseberry, camphor tree, gardenia, cubeb, cumin, cranberry, cola, japanese pepper, sandarac, sandal wood, red sandal wood, perilla, civet, jasmine, ginger, ginseng, cinnamon, starfruit, styrax, spearmint, geranium, thyme, davana, tansy, tangerine, champac, tuberose, camellia, dittany, tolu balsam, tonka beens, nut, jujube, nutmeg, nanten, ti-tree, carrot, violet, pineapple, hibiscus, honey, corn-mint, passion fruit, vanilla, rose, hyssop, hinoki, fusel oil, buchu, peppermint, pepino, verbena, rosewood, popaw, boldo, boronia, pine, mango, bees wax, mimosa, milfoil, musk, maple, melissa, melon, peach, yara-yara, lavender, litsea, linden, rue, wax jambu, rosemary, lovage, and the like.

Further, the other aromatic compositions can be added depending on purposes. Particular examples include aroma of citrus such as orange, lemon, lime, grape fruit, yuzu (*Citrus junos*) and sudachi (*Citrus sudachi*); aroma of berry such as strawberry, raspberry, blue berry; aroma of tropical fruit such as mango, papaya, guava, passion fruit, litchi; aroma of fruit such as apple, grape, pineapple, banana, peach, melon, apricot, ume (*Prunus mume*), and aroma of cherry; aroma of tea and coffee such as green tea, oolong tea, black tea, and coffee; aroma of meat such as beef, pork, and chicken; aroma of herb and spice such as asafetida, ajowan, anise, angelica, fennel, allspice, cinnamon, cassia, chamomile, mustard, cardamom, caraway, cumin, clove, pepper, coriander, sassafras, savory, japanese pepper, perilla, juniperberry, ginger, star anise, horseradish, sage, thyme, tarragon, dill, capsicum, jujube, nutmeg, basil, parsley, marjoram, rosemary, laurel, and wasabi (*Wasabia japonica*); aroma of vegetable such as onion, garlic, green onion, cabbage, carrot, celery, shiitake (*Lentinula edodes*(Berk.) *Pegler*), matsutake (*Tricholoma matsutake*), tomato, burdock, and honewort; aroma of mint such as peppermint, spearmint, and Japanese mint; aroma of vanilla; aroma of nut such as almond, cashew nut, peanut, hazel nut, walnut, chestnut, macadamia nut, pecan nut, pistachio, Brazil nut, and coconut; aroma of liqueur such as wine, whisky, brandy, rum, gin and liqueur; aroma of grain such as corn, potato, sweet potato, cooked rice, and bread; aroma of sugar such as honey, maple syrup, sugar, brown sugar and molasses.

Synthetic fragrances are readily commercially available, and easily synthesized if necessary.

The optically active theaspiran obtained by a method of the present invention is made into an aromatic composition as described above and used for flavoring or perfuming various products. An aromatic composition comprising optically active theaspiran obtained by the production method of the present invention can flavor or fragrance products such as food and beverage, cosmetics, groceries, oral care products, medical products, and the like.

Specific examples of food and beverage include, but not limited to: beverages such as a fruit juice beverage, a fruit wine, milk beverage, a carbonated beverage, a soft drink, and an energy drink; a frozen dessert such as ice cream, sherbet and ice pop; a dessert such as jelly and pudding; an western confectionery such as cake, cookie, chocolate, and chewing gum; a Japanese confectionery such as manju (bun), youkan (adzuki-bean jelly) and uiro (steamed cake); jam; candy; bread; tea drink or soft drink such as green tea, oolong tea, black tea, Japanese persimmon leaf tea, chamomile tea, *Sasa veitchii* tea, mulberry tea, *Houttuynia cordata* tea, pu-erh tea, mate tea, rooibos tea, gymnema tea, guava tea, coffee, and cocoa; soup such as Japanese soup, European soup, and Chinese soup; food seasoning additives, various instant drinks and food; various snack food, and the like.

Examples of cosmetics and groceries which are flavored or perfumed by optically active theaspiran obtained by a production method of the present invention and aromatic composition containing said theaspiran include: a fragrance product, basic skin care, finishing cosmetics, hair cosmetics, tanning cosmetics, medicinal cosmetics, hair care products, soap, body wash, bath agent, detergents, softner, cleaning agent, kitchen detergent, bleaches, aerosol agent, deodorant, fragrant agents, repellant, and other groceries.

More specifically, examples of fragrance product include perfume, eau de parfum, eau de toilette, eau de cologne, and the like; examples of foundation cosmetic include facial cleansing cream, vanishing cream, cleansing cream, cold cream, massage cream, emulsion, skin lotion, essence, pack, makeup remover, and the like; examples of finishing cosmetic include a foundation, face powder, talcum powder, a lip stick, lip balm, cheek rouge, an eye liner, mascara, eye shadow, an eye pencil, eye pack, nail enamel, enamel remover, and the like; and examples of hair cosmetic include pomade, brilliantine, hair dressing, hair stick, a hair solid, a hair treatment, hair cream, hair tonic, hair liquid, hair spay, hair growing agent, hair dye, and the like.

Examples of suntan cosmetics include a suntan product and sunscreen product; examples of medicinal cosmetics include an antiperspirant, an after shave lotion or gel, a permanent wave lotion, medicated soap, medicated shampoo, a medicated skin cosmetics, and the like.

Examples of hair care products include shampoo, rinse, two-in-one shampoo, conditioner, treatment, hair pack, and the like; examples of soaps include face soap, bath soap, fragrant soap, clear soap, synthetic soap, and the like; examples of body cleanser include body soap, body shampoo, hand soap, and the like; examples of bath agent include bath water additives (bath salt, bath tablet, bath liquid, etc.), foam bath (bubble bath, etc.), bath oil (bath perfume, bath capsule, etc.), milk bath, bath jelly, bath cube, and the like; and examples of detergent include heavy-duty detergent for clothes, a light duty detergent for cloths, a liquid detergent, laundry soap, compact washing agent, powder soap, and the like.

Examples of softener include softener, furniture care, and the like; examples of cleaning agent include cleanser, house cleaner, toilet cleanser, bathroom cleaner, glass cleaner, a mold remover, cleansing agent for pipe, and the like.

Examples of kitchen detergent include kitchen soap, synthetic soap for kitchen, detergent for dishes, and the like; examples for bleaches include an oxidative bleaching (chlorine bleaching agent, oxygen bleaching agent, etc.), a reducing bleaching agent (sulfur bleaching agent, etc.), a optical bleaching agent, and the like; examples of aerosol agent include spray type, powder spray, and the like; examples of deodorant fragrant agents include solid type, gel type, liquid type, and the like; examples of groceries include tissue paper, toilet paper, and the like.

Examples of oral care products include toothpaste, buccal wash, mouthwash, troche, chewing gum, and the like; examples of medicinal products include poultice, external drug for skin like ointment, internal agent, and the like.

When optically active theaspiran obtained by the production method of the present invention or an aromatic composition containing said theaspiran is used for flavor or fragrance the above mentioned products, optically active theaspiran or aromatic composition containing the said theaspiran can directly be added to a product depending on the type or the final modes (such as a liquid state, a solid state, a powder state, a gel state, a mist state and an aerosol state) of the products which is flavored or perfumed; optically active theaspiran or aromatic composition containing the said theaspiran which is dissolved in polyols, for example alcohol, propylene glycol and glycerin, to liquefy and the solution can be added; it can also be solubilized or emulsified and dispersed by using a natural gum substance such as gum Arabic, and tragacanth gum or a surface-activating agent (eg. nonionic surfactant such as glycerin fatty acid ester, and sucrose fatty acid ester; an anionic surfactant, a cationic surfactant, an amphoteric surfactant, etc.) and added; it can also be added in film-forming powder form which is formed by a natural gum substance such as gum Arabic, or a excipient such as gelatin and dextrin; or it can also be added in microcapsule form which is formed by capsule-forming agent.

Further, it can also be used by including with inclusion agent such as cyclodextrin, and stabilizing optically active theaspiran or aromatic composition containing the said theaspiran and formulating sustained-release.

The additive amount of the optically active theaspiran can be adjusted depending on the types and forms of products or desired effect or action of the product when the product is flavored. Generally, the additive amount of optically active theaspiran is preferably about 0.0000001-30 wt %, more preferably 0.000001-10 wt % of mass of the product.

The disclosure in Japanese Patent Application No. 2005-264678 can be incorporated in the present invention.

ADVANTAGEOUS EFFECT OF THE INVENTION

To selectively obtain a desired optically active compound was difficult according to conventional methods; however, the present invention provides a method for producing optically active theaspiran which is simple and with at a high purity.

EXAMPLE

The present invention is illustrated by the following examples; however the invention is not limited to the examples and may be modified within the scope of the invention. The condition applied for analysis by gas chromatography (GC) in the following examples is as follows:

Conversion rate:

Column: Neutrabond-1 (0.25 mm×30 m, GL Science Co.)

Temperature rising condition: 100° C. to 220° C. (increase of 10° C. per min)

Optical purity:

Chiral column: CP-Chiralsil-Dex CB (0.25 mm×30 m, Chrompack Co.)

Temperature condition: set at 110° C. (theaspiran), set at 130° C. (intermediate alcohol), set at 140° C. (intermediate ester)<

Example of Synthesis 1

Synthesis of Alcohol (1)

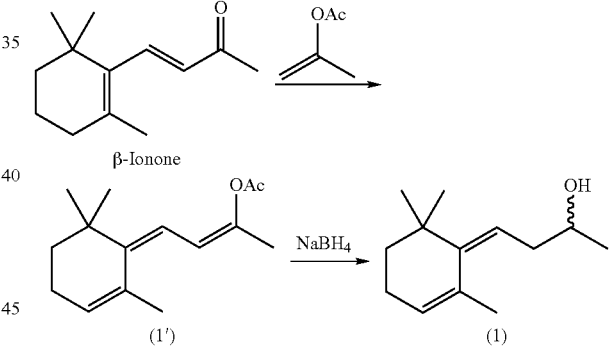

β-Ionone (435.80 g) was dissolved in 1000 mL of isopropenyl acetate, and paratoluenesulfonic acid (2.18 g) was added thereto, then heated under reflux with stirring for 5 hours. The conversion ratio of β-Ionone was confirmed to be 94.7% by gas chromatography (GC) analysis. The reaction solution was cooled to room temperature, and excess isopropenyl acetate was collected under reduced pressure. The resulting crude product was dissolved in toluene and washed with aqueous solution of sodium carbonate. The solvent was distilled from the toluene solution, and enol acetate compound (1') (551.22 g) was obtained. The resulting enol acetate compound (371.90 g) was dissolved in ethanol (1500 ml), and sodium borohydride (63.13 g) was added slowly over 25 min with careful attention to heat. After stirred for 3 hours at room temperature, the conversion ratio was confirmed to be 100% by GC. The reaction solution was poured into a mixture of saturated aqueous ammonium chloride solution-ice, treated in the conventional manner, and the crude product (338.37 g) was obtained. This was purified by distillation using a Claisen distilling column, and the intermediate alcohol compound (1) (262.40 g) was obtained (yield 68.8%).

Example 1

Enantioselective Esterification Using an Enzyme

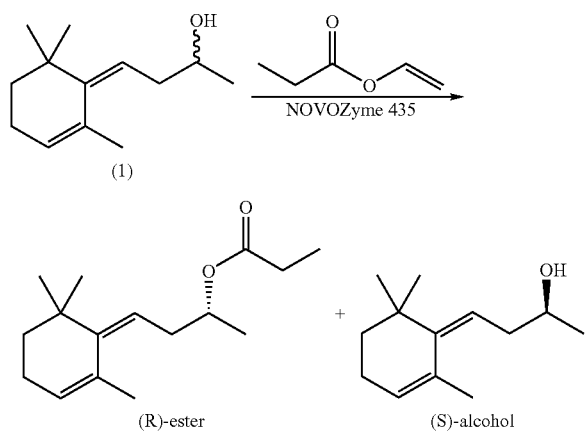

Alcohol compound (1) (19.40 g) and vinyl propionate (3.90 g) were dissolved in toluene (80 ml), and stirred at 35° C. NOVOZyme 435 (0.39 g) was added to the solution, and allowed them to react for 4 hours. The conversion ratio was confirmed to be 43.7% by GC analysis. The optical purity of the resulting ester compound was confirmed to be 99% or more by chiral GC analysis. The reaction solution was separated by decantation, the solvent was distillated under reduced pressure, and crude product (22.27 g) was obtained. The alcohol compound, vinyl propionate and toluene in the same amount as above were added to a flask in which the enzyme remained, and the reaction was carried out at 35° C. in the same manner. After predetermined time of 4 hours, the conversion rate was confirmed to be 45.3%, and the optical purity of the ester compound was confirmed to be 99% or more by the GC analysis. Recycling reaction was performed in the same manner for 4 times, and it was confirmed that the same results were obtained.

Example 2

Hydrolysis of the (R)-Ester Compound

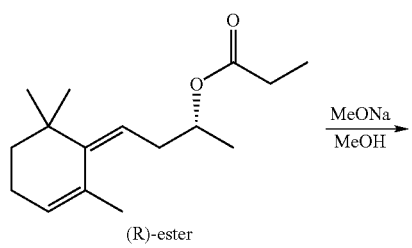

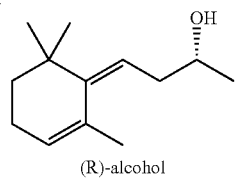

(R)-ester compound (92.25 g) obtained in Example 1 was dissolved in methanol (300 ml), and the mixture was stirred at room temperature. Then, 28% sodium methylate/methanol solution (85.43 g) was added slowly with careful attention to heat. Then the reaction was allowed to proceed for 2 hours at room temperature, and the conversion rate was confirmed to be 98.7% by GC. The reaction solution was poured into water, extracted with toluene and treated in the conventional manner. Crude product (74.99 g) was obtained. The optical purity of the product was confirmed to be 96% e.e. by the chiral GC.

Example 3

Production of (2R)-Theaspiran by Ring Closure

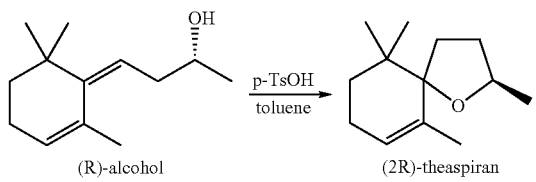

Crude (R)-alcohol compound (74.99 g) obtained in Example 2 was dissolved in toluene (750 mL), and the solution was heated at 80° C. with stirring. Paratoluenesulfonic acid (p-TsOH) (1.50 g) was added thereto and the reaction was allowed to proceed at the same temperature for 3 hours. The conversion rate was confirmed to be 99.3% by GC analysis. The reaction solution was cooled to room temperature, and washed with an aqueous solution of sodium carbonate. The solvent was collected from the organic layer, and crude theaspiran (86.93 g) was obtained. To the resulting crude theaspiran BHT (0.87 g) was added, and then purified by distillation using a Sulzer distilling column, and (2R)-theaspiran (55.0 g) was obtained (yield 76.8%). Resulting (2R)-theaspiran had strong fruity flavor.

Example 4

Production of (2S)-Theaspiran by Ring Closure

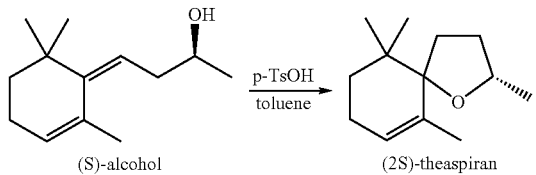

(S)-alcohol compound (69.92 g) obtained in Example 1 (the optical purity: 80% e.e.) was dissolved in toluene (700 ml), and the solution was heated to 80° C. with stirring. Paratoluenesulfonic acid (1.40 g) was added and the reaction was allowed to proceed at the same temperature for 3 hours. The conversion rate was confirmed to be 100% by GC analysis. The reaction solution was cooled to room temperature, and washed with an aqueous solution of sodium carbonate. The solvent was collected from the organic layer, and crude theaspiran (70.95 g) was obtained. To resulting crude theaspiran BHT (0.70 g) was added, and then it was purified by distillation using a Sulzer distilling column, and (2S)-theaspiran (49.6 g) was obtained (yield 71.0%). The resulting (2S)-theaspiran had a camphor-like, woody-like and eucalyptus-like flavor.

Synthesis Example 2

Synthesis of Propionate of Racemic Alcohol (1)

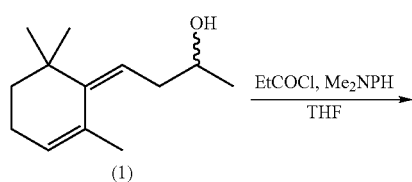

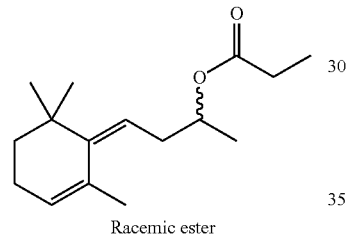

To racemic alcohol compound (1) (181.89 g, 0.94 mol) in a 2 L four-necked flask, THF (900 mL) and N,N-dimethyl aniline (130.8 mL, 1.034 mol) were added, and propionyl chloride (95.42 g, 1.034 mol) was added dropwise. The reaction was allowed to proceed in water bath at 40° C. for 5 hrs. Then, the reaction mixture was poured on ice water, and the organic layer was extracted with toluene. The extracted solution was condensed, and crude product (238.21 g) was obtained. Desired propionate (152.33 g) was obtained by Claisen distillation (yield 65.0%).

Example 5

Optical Resolution of the Racemate with Enzyme

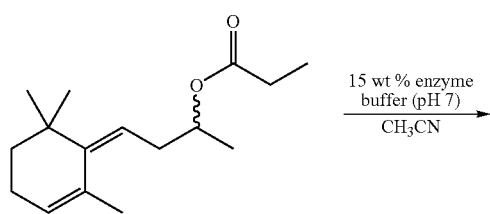

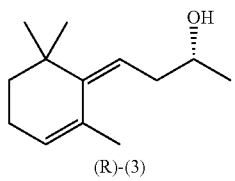

To propionate (65.77 g, 0.25 mol) obtained in Synthesis Example 2 in a 1 L flask with a vane stirrer, acetonitrile (300 mL) and buffer solution (pH 7, 30 mL) were added and dissolved, and stirred. Enzyme NOVOZyme 435 (9.87 g, 15 wt %) was added thereto, and the reaction was allowed to proceed at 50° C. in water bath for 17.5 hours. The conversion rate of the reaction was confirmed to be 32.5% by GC. The enzyme was filtered out from the reaction solution, and the solution was extracted with toluene and condensed. The resulting crude product (65.59 g) was purified by distillation using a Sulzer distilling column, and (R)-alcohol compound (16.28 g) was obtained (yield 33.7%). The optical purity was confirmed to be 98% e.e. or more by chiral GC analysis.

Example 6

Production of (2R)-Theaspiran by Ring Closure

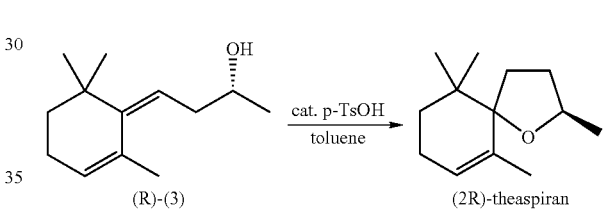

To (R)-alcohol compound (16.28 g, 84 mmol) in a 300 mL four-necked flask, toluene (160 mL) and p-TsOH (380 mg) were added, and the reaction was allowed to proceed at 80° C. for 3 hours on heating. The conversion rate was confirmed to be 100%. The reaction solution was cooled to room temperature, and washed with 5% aqueous solution of sodium carbonate. Then, the resulting crude product (17.21 g) was purified by the Cleisen distillation, and (2R)-theaspiran (7.8 g) of chemical purity of 98% or higher was obtained (yield 48%). According to chiral GC analysis, the optical purity of the product was confirmed to be 94% e.e. with respect to the asymmetry carbon of position 2 attached with methyl group.

Example 7

Passion fruit-like flavor compositions shown in Table 1 were prepared by using the (2S)-theaspiran synthesized in Example 4.

TABLE 1

| Component | Parts by weight |
| --- | --- |
| (2S)-theaspiran synthesized in Ex. 4 | 1.000 |
| Octanol | 1.000 |
| cis-3-hexenol | 10.000 |
| Ethyl butyrate | 30.000 |
| Ethyl hexanoate | 40.000 |
| Hexyl acetate | 5.000 |
| Hexyl hexanoate | 5.000 |
| γ-decalactone | 0.100 |

TABLE 1-continued

| Component | Parts by weight |
|---|---|
| 2-phenyl ethyl alcohol | 0.200 |
| Linalool | 0.500 |
| Furaneol (Trade name of Firmenich Co.) | 1.000 |
| Hexanoic acid | 5.000 |
| β-damascone | 0.020 |
| 2-methyl-4-propyl-1,3-oxathiane | 0.300 |
| 8-mercapto menthone | 0.005 |
| Propylene glycol (solvent) | 900.875 |
| Total | 1000.000 |

Comparison Example 1

A passion fruit-like flavor composition was prepared by using the racemic form of theaspiran instead of (2S)-theaspiran shown in Table 1 of Example 7.

Test Example 1

With respect to the passion fruit like flavor compositions of Example 7 and Comparison Example 1, the sensory evaluation was carried out by 10 panelists who have experienced more than 5 years in training. As a result, all of the panelists evaluated that the composition of Example 7 has rich fruity character and provided a natural and fleshy sensation compared with the composition of Comparison Example 1.

Example 8

A raspberry-like flavor composition shown in Table 2 was prepared by using the (2R)-theaspiran synthesized in Example 3.

TABLE 2

| Component | Parts by weight |
|---|---|
| (2R)-Theaspiran synthesized in Ex. 3 | 1.000 |
| Trans-2-hexenal | 5.000 |
| Ethyl butyrate | 30.000 |
| Isoamyl acetate | 3.000 |
| Isobutyl acetate | 9.000 |
| Trans-2-hexenyl acetate | 3.000 |
| γ-decalactone | 1.000 |
| Linalool | 3.000 |
| Furaneol (Trade name of Firmenich Co.) | 2.000 |
| 2-methyl butyric acid | 30.000 |
| α-Ionon | 3.000 |
| β-damascenone | 1.000 |
| Dimethyl sulfide | 1.000 |
| Raspberry ketone | 60.000 |
| Propylene glycol (solvent) | 848.000 |
| Total | 1000.000 |

Comparison Example 2

A raspberry-like flavor composition was prepared by using the racemic form of theaspiran instead of (2R)-theaspiran shown in Table 2 of Example 8.

Test Example 2

With respect to the raspberry-like flavor compositions of Example 8 and Comparison Example 2, the sensory evaluation was carried out by 10 panelists who have experienced more than 5 years in training. As a result, all of the panelists evaluated that the composition of Example 9 has stronger sensation of fresh, and has a natural, fresh and juicy sensation compared with the composition of Comparison Example 2.

Example 9

A rose-like fragrance composition shown in Table 3 was prepared by using the (2R)-theaspiran synthesized in Example 3.

TABLE 3

| Composition | Parts by weight |
|---|---|
| Allyl heptanoate | 0.5 |
| Benzyl acetate | 1.5 |
| Citronellol | 6.5 |
| Citronellyl acetate | 0.3 |
| Galaxolide (trade name of IFF Co.) 50 BB | 5.0 |
| Geraniol | 5.0 |
| Hedione (trade name of Firmenich Co.) | 15.0 |
| Cis-3-hexenol | 0.3 |
| Hexyl acetate | 2.0 |
| β-Ionon | 2.5 |
| Lemon oil california | 2.0 |
| Linalool | 6.0 |
| Methyl iso-eugenol | 1.2 |
| Musk T (trade mark of Takasago Int'l. Corp.) | 3.0 |
| Nerol pure | 2.0 |
| Phenyl acetaldehyde 50% BB | 0.5 |
| Phenethyl alcohol | 35.0 |
| Phenethyl salicylate | 4.0 |
| Raspberry ketone 10% DPG | 1.0 |
| L-rose oxide 10% DPG | 1.0 |
| Rosephenone | 4.0 |
| (2r)-Theaspiran synthesized in Ex. 3 | 0.2 |
| Thesaron (trade mark of Takasago Int'l. Corp.) | 0.5 |
| γ-undecalactone | 1.0 |
| Total | 100.0 |

Example 10

To a drink comprising 5.3% of the mixed liquid of fructose and glucose (solid portion: 75%), 0.05% of citric acid and 0.03% of sodium citrate, flavor composition obtained in Example 7 was added at 0.01%, which resulted in a drink superior in flavor balance, and high natural taste, fruit juice sensation and fruity feel compared to a the drink to which the flavor composition obtained in Comparison Example 1 was added.

Example 11

Preparation of a carbonated beverage comprising 7.5% of sugar, 5% of the mixed liquid of fructose and glucose (solid portion: 75%), 0.15% of citric acid and 0.01% of the flavor composition obtained in Example 8 according to an ordinary method, a carbonated beverage having excellent refreshing and fresh sensations and a good taste could be obtained in comparison with the addition of the flavor composition obtained in Comparison Example 2.

Example 12

100 g of shampoo containing 0.5% of the fragrance composition of Example 9 was produced according to the formulation given in Table 4.

TABLE 4

| Component | Parts by weight |
|---|---|
| Polyoxyethylene lauryl ether sodium sulfate | 14 |
| Amide propyl betaine laurate | 4 |
| Palm oil fatty acid diethanol amide | 3 |
| Cationated cellulose | 0.5 |
| Ethyleneglycol di-stearate | 1 |
| Para-oxybenzoic acid ester | 0.25 |
| Citric acid | qs |
| Fragrance and flavor composition obtained in Ex. 9 | 0.5 |
| Purified water | Remaining portion |
| Total | 100 |

The invention claimed is:

1. A method for producing optically active theaspiran represented by the formula(4*),

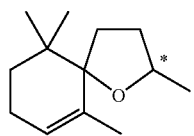

(4*)

wherein * indicates asymmetric carbon atom;
the method is characterized in that mixture of optical isomers of alcohol represented by the formula(1);

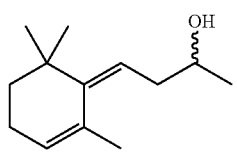

(1)

is enantioselectively esterified in the presence of an enzyme by an esterification agent of the general formula (2),

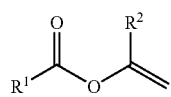

(2)

wherein $R^1$ is a hydrogen atom or $C_1$-$C_6$ hydrocarbon group optionally having a substituent group, and $R^2$ is a hydrogen atom, $C_1$-$C_6$ alkyl group or $C_1$-$C_4$ alkoxy group;
and optically active ester represented by the general formula (3*) and/or optically active alcohol represented by the formula (1*) is obtained,

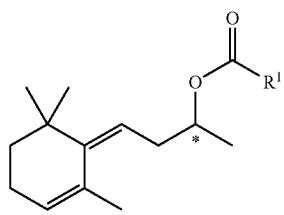

(3*)

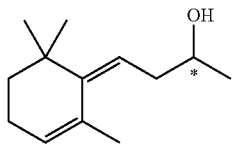

(1*)

wherein $R^1$ is a hydrogen atom or a $C_1$-$C_6$ hydrocarbon group optionally having a substituent group; wherein * indicates an asymmetric carbon atom; and the abundance ratio of R-form and S-form of the formula 3* and said ratio of the formula 1* are different from each other, one contains more R-form and the other contains more S-form) the resulting optically active alcohol (1*) is isolated, and the alcohol (1*) is cyclized by an acid catalyst.

2. A method for producing optically active theaspiran represented by the formula (4*), wherein * indicates an asymmetric carbon atom:

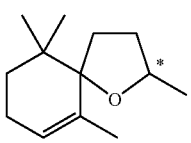

(4*)

the method is characterized in that the optically active ester represented by the general formula (3*) which is obtained by the method of claim 1 is isolated, hydrolyzed and cyclized by an acid catalyst.

3. A method for producing optically active theaspiran represented by the formula (4*),

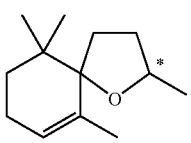

(4*)

wherein * indicates an asymmetric carbon atom;
the method is characterized in that mixture of optical isomers of ester represented by the formula(3),

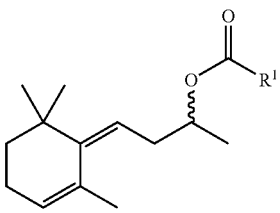

(3)

wherein $R^1$ is a hydrogen atom or a $C_1$-$C_6$ hydrocarbon group optionally having a substituent group:
is enantioselectively hydrolyzed in the presence of an enzyme, and optically active ester represented by the general formula (3*) and/or optically active alcohol represented by the formula (1*) is obtained,

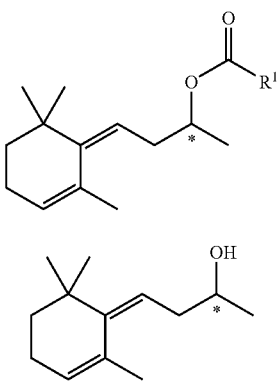

(3*)

(1*)

wherein R¹ is a hydrogen atom or a $C_1$-$C_6$ hydrocarbon group optionally having a substituent group; wherein * indicates an asymmetric carbon atom; and the abundance ratio of R-form and S-form of the formula (3*) and said ratio of the formula (1*) are different from each other, one contains more R-form and the other contains more S-form;

the resulting optically active alcohol of the formula (1*) is isolated, and the alcohol (1*) is cyclized by an acid catalyst.

4. A method for producing an optically active theaspiran represented by the formula (4*) wherein * indicates an asymmetric carbon atom,

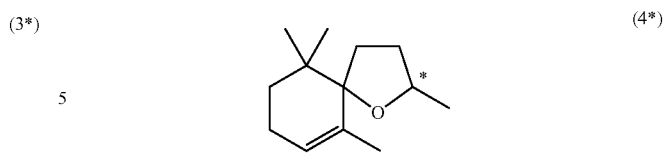

(4*)

the method is characterized in that the optically active ester represented by the general formula (3*) which is obtained by the method of claim 3 is isolated and hydrolyzed, and then cyclized by the acid catalyst.

5. The method for producing an optically active theaspiran according to any of one of claims 1 through 4 wherein the enzyme is lipase.

6. An aromatic composition comprising an optically active theaspiran produced according to a method of any one of claims 1 through 4, the optically active theaspiran present in an amount of 0.000001-10 wt %.

7. A food, beverage, cosmetic or grocery item comprising an aromatic composition according to claim 6.

8. A method for producing an aromatic composition, the method comprising:
providing an optically active theaspiran produced according a method of any one of claims 1 through 4;
mixing the theaspiran a carrier.

9. A method for producing a food, beverage, cosmetic or grocery item, the method comprising:
producing an optically active theaspiran by a method of of any one of claims 1 through 4 and the adding the said optically active theaspiran to the item.

* * * * *